(12) United States Patent
Frost

(10) Patent No.: US 7,135,569 B2
(45) Date of Patent: Nov. 14, 2006

(54) PROCESS FOR THE PREPARATION OF PYRIDINYL AND PYRIMIDINYL MONO-FLUORINATED BETA KETO-ESTERS

(75) Inventor: Jonathan Frost, Wissous (FR)

(73) Assignee: Sanof I-Aventis, Paris (FR)

( * ) Notice: Subject to any disclaimer, the term of this patent is extended or adjusted under 35 U.S.C. 154(b) by 0 days.

(21) Appl. No.: 11/221,023

(22) Filed: Sep. 7, 2005

(65) Prior Publication Data

US 2006/0058526 A1 Mar. 16, 2006

Related U.S. Application Data

(63) Continuation of application No. PCT/EP2004/003052, filed on Mar. 5, 2004.

(30) Foreign Application Priority Data

Mar. 7, 2003 (EP) .................... 03290568

(51) Int. Cl.
*C07D 239/26* (2006.01)
*C07D 213/127* (2006.01)
(52) U.S. Cl. ...................... 544/298; 546/302
(58) Field of Classification Search ................ 544/298; 546/302
See application file for complete search history.

(56) References Cited

FOREIGN PATENT DOCUMENTS

EP 1295885 A1 * 3/2003
WO WO 03/027116 4/2003

OTHER PUBLICATIONS

Linderman, R.J., et. al., Oxidation of Fluoroalkyl-Substituted Carbinols by the Dess-Martin Reagent, Journal of Organic Chemistry, vol. 54, No. 3, pp. 661-668 (1989).
Thenappan, A., et. al., An Expedient Synthesis of A-Fluoro-B-Ketoesters1, Tetrahedron Letters, vol. 30, No. 45 (1989) pp. 6113-6116.

* cited by examiner

Primary Examiner—Venkataraman Balasubramanian
(74) Attorney, Agent, or Firm—Balaram Gupta

(57) ABSTRACT

The present invention relates to a process for preparing pyridinyl and pyrimidinyl mono-fluorinated beta keto esters of formula (I):

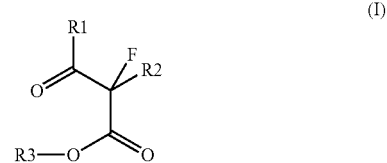

wherein:

R1 represents a pyridine ring or a pyrimidine ring, the rings being optionally substituted by a $C_{3-6}$ cycloalkyl group, a $C_{1-4}$ alkyl group, a $C_{1-4}$ alkoxy group, a benzyl group or a halogen atom;

R2 represents a hydrogen atom, a $C_{1-6}$ alkyl group or ahalogenatom; and

R3 represents a $C_{1-6}$ alkyl group; by reacting with fluorine a compound of formula (II)

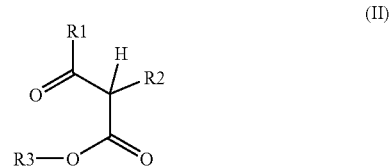

wherein R1, R2 and R3 have the same meaning as defined above.

10 Claims, No Drawings

PROCESS FOR THE PREPARATION OF PYRIDINYL AND PYRIMIDINYL MONO-FLUORINATED BETA KETO-ESTERS

This application is a continuation of International Application No. PCT/EP2004/003052, filed Mar. 5, 2004, which claims the benefit of priority of European Patent Application No. EP 03290568.9 filed Mar. 7, 2003.

The present invention relates to a process for preparing pyridinyl and pyrimidinyl mono-fluorinated beta keto esters, useful as intermediates for pharmaceutical compounds.

Accordingly an object of the present invention is to provide a process for preparing pyridinyl and pyrimidinyl mono-fluorinated beta keto esters of formula (I):

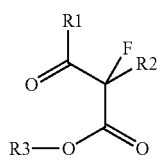

(I)

wherein:
R1 represents a pyridine ring or a pyrimidine ring, the rings being optionally substituted by a $C_{3-6}$ cycloalkyl group, a $C_{1-4}$ alkyl group, a $C_{1-4}$ alkoxy group, a benzyl group or a halogen atom;
R2 represents a hydrogen atom, a $C_{1-6}$ alkyl group or a halogen atom; and
R3 represents a $C_{1-6}$ alkyl group; by reacting with fluorine gas a compound of formula (II)

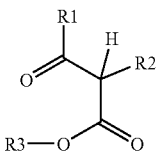

(II)

wherein R1, R2 and R3 have the same meaning as defined above.

As a further object of the present invention there is provided compounds of formula (I), wherein R1, R2 and R3 have the same meaning as defined above with the proviso that compounds of formula (I) is not the ethyl 2-fluoro-3-oxo-3-pyridin-4-yl propanoate.

Compounds of formula (I) can comprise one or more asymmetric carbon atoms. They can therefore exist in the form of enantiomers or diastereoisomers. These enantiomers and diastereoisomers, as well as their mixtures, including racemic mixtures, form part of the invention.

The compounds of formula (I) can be provided in the form of a free base or in the form of addition salts with acids, which also form part of the invention. These salts might be prepared according to well known methods in the art.

The compounds of formula (I) might be useful as intermediates for pharmaceutical compounds such as described in PCT/EP02/11127 and PCT/EP02/11128.

According to the present invention, the terms below have the following meanings:
a pyridine ring represents a 2, 3 or 4-pyridinyl group;
a pyrimidine ring represents a 2, 4 or 5-pyrimidinyl group;
a halogen atom corresponds to a chlorine, bromine or iodine atom;
a $C_{1-6}$ alkyl group represents a straight or branched alkyl group having 1 to 6 carbon atoms, for example, methyl group, ethyl group, n-propyl group, isopropyl group, n-butyl group, isobutyl group, sec-butyl group, tert-butyl group, n-pentyl group, isopentyl group, neopentyl group, 1,1-dimethylpropyl group, n-hexyl group, iso-hexyl group, and the like;
a $C_{3-6}$ cycloalkyl group corresponds to a cyclic alkyl, having from 3 to 6 carbon atoms. The following examples may be cited: cyclopropyl, methylcyclopropyl, cyclobutyl, and
an alkoxy group corresponds to an —O-alkyl group, wherein the alkyl group is as defined above.

According to another object of the invention, the process of the present invention is carried out for the compounds of formula (I) wherein:
R1 represents a 3 or 4-pyridinyl group and more preferably a 4-pyridinyl group; or a 4- or 5-pyrimidinyl group and more preferably 4-pyrimidinyl group, the rings being optionally substituted by a $C_{1-2}$ alkyl group, and/or
R2 represents a hydrogen atom or a $C_{1-3}$ alkyl group; and/or
R3 represents a $C_{1-3}$ alkyl group;

and more preferably for the compounds of formula (I) wherein:
R1 represents an unsubstituted 4-pyridinyl group or 4-pyrimidinyl group; and/or
R2 represents a hydrogen atom; and/or
R3 represents a methyl group.

According to a further object the process of the invention is carried out for the compounds of formula (I):
ethyl 2-fluoro-3-oxo-3-pyridin-4-yl propanoate and
ethyl 2-fluoro-3-oxo-3-pyrimidin-4-yl propanoate.

In accordance with the present invention, the process of fluorination may be carried out following scheme 1.

Scheme 1:

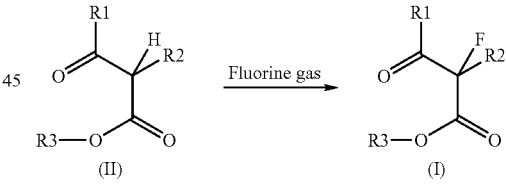

In scheme 1 starting compound (II) and reactants, unless otherwise indicated, are commercially available or described in literature, or can be prepared according to methods described in literature or known to one of skill in the art.

For example compound of formula (II) may be prepared according to methods described in PCT/EP02/11127 and PCT/EP02/11128.

According to scheme 1, compound of formula (II), wherein R1, R2 and R3 are as defined for compound of formula (I), may be fluorinated using fluorine gas in the presence of one or more acids. The acids being best chosen from formic acid, trifluoroacetic acid, sulfuric acid, trifluoromethanesulfonic acid and hydrofluoric acid. The reaction may be carried in the absence or in the presence of an inert solvent such as acetonitrile or chloroform. Preferably the reaction is carried out in the presence of hydrofluoric acid in absence of any solvent.

The fluorine gas, used in the present invention, is preferably diluted with an inert gas such as nitrogen or helium. The concentration of fluorine in inert gas is ranging from 1 to 50 percent, preferably 2 to 25 percent and more preferably 5 to 15 percent by volume. The ratio of fluorine to compound (II) depends on the conditions of the experiments. The molar ratio may range for example from 0.5 to 2, more preferably form 0.7 to 1.5 (fluorine compound (II)).

The reaction may be carried out at temperatures ranging from −78° C. to 50° C., preferably from −50° C. to 0° C. and more preferably from −25° C. to −7° C.

Compounds of formula (I) may be isolated and purified according to well-known methods in the art. For example when the hydrofluoric acid is used, the excess of acid may be removed by evaporation. The excess of acid may be neutralised and followed by extraction and distillation.

As a further object of the present invention there is provided compounds of formula (I), wherein R1, R2 and R3 have the same meaning as defined above with the proviso that compounds of formula (I) is not the ethyl 2-fluoro-3-oxo-3-pyridin-4-yl propanoate. More particularly compound of formula (I) is the ethyl 2-fluoro-3-oxo-3-pyrimidin-4-yl propanoate. These compounds are useful as intermediates for preparing pharmaceutical compounds such as the GSK3beta inhibitors described in PCT/EP02/11127 and PCT/EP02/11128.

The following examples describe the process according to the invention. These examples are not intended to be limitative and only illustrate the present invention.

EXAMPLE 1

Ethyl 2-fluoro-3-oxo-3-pyridin-4-yl propanoate 1.1. Procedure A

Ethyl 3-oxo-3-pyridin-4-yl propanoate (49.13 g, 0.25 moles) was charged into anhydrous hydrogen fluoride (AHF) (440 g) with cooling. Fluorine in nitrogen (10%) (67 liters, 0.28 moles, 1.12 equivalents) was passed through the mixture in a −20° C. ice bath over the course of 325 minutes. AHF was largely removed by evaporation followed by standing under vacuum. This resulted in a brown semi-solid. The crude mixture was added to saturated sodium carbonate solution (800 ml), adding more solid carbonate as required. The solution was extracted with methylene chloride (4×500 ml). Extracts were combined and dried (MgSO$_4$). Removal of solvents under reduced pressure gave a brown oil (45 g).

Gas chromatography indicates 90% of ethyl 2-fluoro-3-oxo-3-pyridin-4-yl propanoate.

1.2. Procedure B

Ethyl 3-oxo-3-pyridin-4-yl propanoate (340.1 g, 1.76 moles) was charged onto anhydrous hydrogen fluoride (AHF) (7.0 kg) with cooling and stirring. Fluorine in nitrogen (10%) (420 liters, 1.75 moles, 1.0 equivalent) was passed through the stirred mixture cooled to −9° C. over the course of 130 minutes. A sample was taken from the reactor, worked up, and analysed, indicating complete conversion of the starting material.

The AHF was removed by evaporation. The resulting liquid (613 g) was removed into a vessel. The vessel was washed with saturated sodium carbonate solution. These washings were used in the neutralisation of remain product. Further evaporation of the crude product under nitrogen overnight caused 60 g of HF to evaporate. The product mixture was neutralised with sodium carbonate and water. More water was added to bring volume to 9 liters. The mixture was extracted, in portions, with methylene chloride (effectively 5×2 liters). Extracts were combined, dried (MgSO$_4$), and solvents were removed yielding brown liquid (218.5 g).

Gas chromatography analysis indicates 88% of ethyl 2-fluoro-3-oxo-3-pyridin-4-yl propanoate.

1.3. Distillation of Crude Product

The ethyl 2-fluoro-3-oxo-3-pyridin-4-yl propanoate (397.6 g-containing some solvent) were combined and distilled under vacuum (125° C. head temperature, 0.12 mbar–0.4 mbar). Weight of product recovered is 258.4 g.

Gas chromatography analysis indicates 83% of ethyl 2-fluoro-3-oxo-3-pyridin-4-yl propanoate. On standing the mixture starts to crystallise.

EXAMPLE 2

Ethyl 2-fluoro-3-oxo-3-pyrimidin-4-yl propanoate

Ethyl 3-oxo-3-pyrimidin-4-yl propanoate (9.98 g, 0.051 moles) was charged onto anhydrous hydrogen fluoride (AHF) (130 g) with cooling. Fluorine in nitrogen (10%) (19 liters, 0.079 moles, 1.54 equivalents) was passed through the mixture at −20° C. ice bath over the course of 1.5 hours. Fluorination was stopped at this time as sample analysis indicated that the reaction was complete (gas chromatography analysis of worked up sample indicates 72% of ethyl 2-fluoro-3-oxo-3-pyrimidin-4-yl propanoate). AHF was largely removed by evaporation followed by standing under vacuum. This resulted in a brown solid (13.9 g). Water was added followed by sodium carbonate to neutralise with cooling. The solution was extracted with methylene chloride (3×250 ml). Extracts were combined and dried (MgSO$_4$). Removal of solvents under reduced pressure gave a brown oil (3.35 g).

The final product was recovered following the method described in example 1.3.

What is claimed is:

1. A process for the preparation of pyridinyl or pyrimidinyl mono-fluorinated beta keto esters of formula (I):

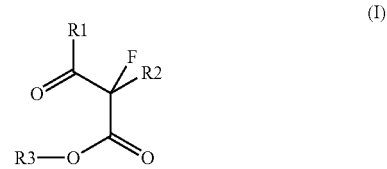

wherein:

R1 represents a pyridine ring or a pyrimidine ring, wherein the rings are optionally substituted by $C_{3-6}$ cycloalkyl, $C_{1-4}$ alkyl, $C_{1-4}$ alkoxy, benzyl or halogen;

R2 represents hydrogen, $C_{1-6}$ alkyl or halogen; and

R3 represents $C_{1-6}$ alkyl;

comprising:

reacting with fluorine gas a compound of formula (II) in the presence of one or more acids,

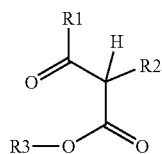

wherein R1, R2 and R3 have the same meaning as defined above.

2. The process according to claim 1, wherein the acid is chosen from formic acid, trifluoroacetic acid, sulfuric acid, trifluoromethanesulfonic acid and hydrofluoric acid.

3. The process according to claim 2, wherein the reaction is carried out in the absence of solvent.

4. The process according to claim 2, wherein the reaction is carried out in the presence of an inert solvent, wherein said solvent is acetonitrile or chloroform.

5. The process according to claim 3, wherein the reaction is carried out in the presence of hydrofluoric acid in absence of solvent.

6. The process according to claim 1, wherein:
R1 represents a 3 or 4-pyridinyl or a 4- or 5-pyrimidinyl, optionally substituted by a $C_{1-2}$ alkyl group, and
R2 represents hydrogen or $C_{1-3}$ alkyl; and
R3 represents $C_{1-3}$ alkyl.

7. The process according to claim 1, wherein the compound of formula (I) is: ethyl 2-fluoro-3-oxo-3-pyridin-4-yl propanoate or ethyl 2-fluoro-3-oxo-3-pyrimidin-4-yl propanoate.

8. A compound of formula (I):

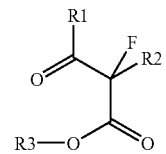

wherein
R1 represents a pyridine ring or a pyrimidine ring, wherein the rings are optionally substituted by $C_{3-6}$ cycloalkyl, $C_{1-4}$ alkyl, $C_{1-4}$ alkoxy, benzyl or halogen;
R2 represents hydrogen, C1–6 alkyl or halogen; and
R3 represents C1–6 alkyl; with the proviso that compound of formula (I) is not ethyl 2-fluoro-3-oxo-3-pyridin-4-yl propanoate.

9. The compound according to claim 8 which is ethyl 2-fluoro-3-oxo-3-pyrimidin-4-yl propanoate.

10. The compound according to claim 8 wherein R1 is an optionally substituted pyrimidine ring.

* * * * *